United States Patent
Avinash et al.

(10) Patent No.: US 6,343,111 B1
(45) Date of Patent: Jan. 29, 2002

(54) DUAL ENERGY DECOMPOSITION USING AUTOMATICALLY DETERMINED CANCELLATION PARAMETERS

(75) Inventors: Gopal B. Avinash, New Berlin, WI (US); Jianguo Zhao, Watervliet, NY (US); Francois Serge Nicolas, Wauwatosa; Kenneth Scott Kump, Waukesha, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/657,033

(22) Filed: Sep. 7, 2000

(51) Int. Cl.$^7$ ................................................ H05G 1/08
(52) U.S. Cl. ..................... 378/98.11; 378/98.9; 378/5
(58) Field of Search ......................... 378/4, 5, 16, 62, 378/98.11, 98.9

(56) References Cited

U.S. PATENT DOCUMENTS

| | | | | |
|---|---|---|---|---|
| 4,542,459 A | * | 9/1985 | Riederer | 600/431 |
| 5,115,394 A | * | 5/1992 | Walters | 382/131 |
| 5,648,997 A | * | 7/1997 | Chao | 378/98.4 |
| 5,771,269 A | * | 6/1998 | Chao | 378/5 |
| 5,931,780 A | * | 8/1999 | Giger et al. | 600/407 |
| 6,052,433 A | * | 4/2000 | Chao | 378/98.9 |
| 6,173,034 B1 | * | 1/2001 | Chao | 378/98.8 |

* cited by examiner

Primary Examiner—David V. Bruce
(74) Attorney, Agent, or Firm—McAndrews, Held & Malloy, Ltd.; Peter J. Vogel; Michael A. Dellapenna

(57) ABSTRACT

A method for determining a suggested value for a cancellation parameter for a dual energy decomposition includes obtaining a first energy level image of internal structure, obtaining a second, lower, energy level image of the internal structure, and iteratively processing the images to determine a provisional value for the cancellation parameter. The iteration includes varying a cancellation parameter in a cancellation equation, obtaining a structure cancelled image from the first and second energy level images according to the cancellation equation, and evaluating a cancellation metric from the structure cancelled image. The provisional cancellation parameter may then be chosen (e.g., as the value that approximately minimizes a variance cancellation metric). Further iterations may be performed around the provisional cancellation parameter to refine the provisional cancellation parameter into a final cancellation parameter.

36 Claims, 2 Drawing Sheets

DUAL ENERGY DECOMPOSITION USING AUTOMATICALLY DETERMINED CANCELLATION PARAMETERS

BACKGROUND OF THE INVENTION

The present invention relates to medical diagnostic X-ray imaging. In particular, the present invention relates to dual energy decomposition for tissue specific imaging using a computer assisted detection technique to obtain a cancellation parameter.

Today, doctors and technicians commonly have access to very sophisticated medical diagnostic X-ray imaging devices. Typically during the operation of an X-ray imaging device, an X-ray source emits X-ray photons under very controlled circumstances. The X-ray photons travel through a region of interest (ROI) of a patient under examination and impinge upon a detector. In the past, X-ray imaging devices employed rudimentary film based detectors. However, recent developments have led to solid state detectors comprised of a grid of discrete detector elements that individually respond to exposure by X-ray photons. Regardless of the detector used, however, the goal remain s the same, namely, to produce a clear resultant image of preselected structures of interest (e.g., specific types of tissues) within the ROI.

There is an inherent difficulty associated with producing a clear resultant image, however. In particular, because the X-ray photons travel through the entire patient, the image formed on the detector is a superposition of all the anatomic structures through which X-ray photons pass, including the preselected structures of interest. The superposition of anatomic structures is sometimes referred to as "anatomic noise". The effect of anatomic noise on the resultant image is to produce clutter, shadowing, and other obscuring effects that render the resultant image much less intelligible than the ideal clear resultant image.

Past attempts to reduce the effects of anatomic noise included, for example, "dual-energy" imaging. When employing dual-energy imaging, a doctor or technician acquired an image at high average X-ray photon energy, and an image at low average X-ray photon energy. Because different internal structures absorb different X-ray photon energies to different extents, it was possible to combine the two resultant images to suppress anatomic noise, according to:

$$SB(x,y)=\exp[\log (H(x,y))-w \log(L(x,y))], (0<w<1),$$

where SB is the decomposed image achieved through the log subtraction at a specific cancellation parameter w, H(x,y) is an image obtained at high energy, and L(x,y) is an image obtained at low energy. By varying w, SB becomes a decomposed image of either soft tissue or of bone.

However, in the past, users of the previously mentioned decomposition technique had to vary the cancellation parameter, w, manually through trial and error. The resulting manual variation of the cancellation parameter was time consuming and hindered the workflow in the clinical environment. Furthermore, the final value chosen for the cancellation parameter was not always the one that provided the best cancellation of bone or soft tissue given the high and low energy images.

A need has long existed in the industry for a method and apparatus for dual energy decomposition that addresses the problems noted above and previously experienced.

BRIEF SUMMARY OF THE INVENTION

A preferred embodiment of the present invention provides a method for determining a suggested value for a cancellation parameter for a dual energy decomposition. The method includes obtaining a first energy level image of internal structure, obtaining a second, lower, energy level image of the internal structure, and iteratively processing the images to determine a provisional value for the cancellation parameter. In particular, the iteration includes varying a cancellation parameter in a cancellation equation, obtaining a structure cancelled image from the first and second energy level images according to the cancellation equation, and evaluating a cancellation metric from the structure cancelled image. The provisional cancellation parameter may then be chosen (e.g., as the value that approximately minimizes a variance cancellation metric). Further iterations may be performed around the provisional cancellation parameter to refine the provisional cancellation parameter into a final cancellation parameter.

Similarly, the present invention may be embodied in a medical diagnostic imaging processing system. The system includes a processing circuit, and a memory coupled to the processing circuit for storing a first energy level image of internal structure and a second, lower, energy level image of the internal structure. The memory stores instructions for execution by the processor to accomplish the steps noted above. In particular, the instructions iteratively vary a cancellation parameter in a cancellation equation, obtain a structure cancelled image from the first and second energy level images according to the cancellation equation, and evaluate a cancellation metric from the structure cancelled image. The instructions then select a provisional cancellation parameter based on the cancellation metric.

DETAILED DESCRIPTION OF THE INVENTION

Figure 1:
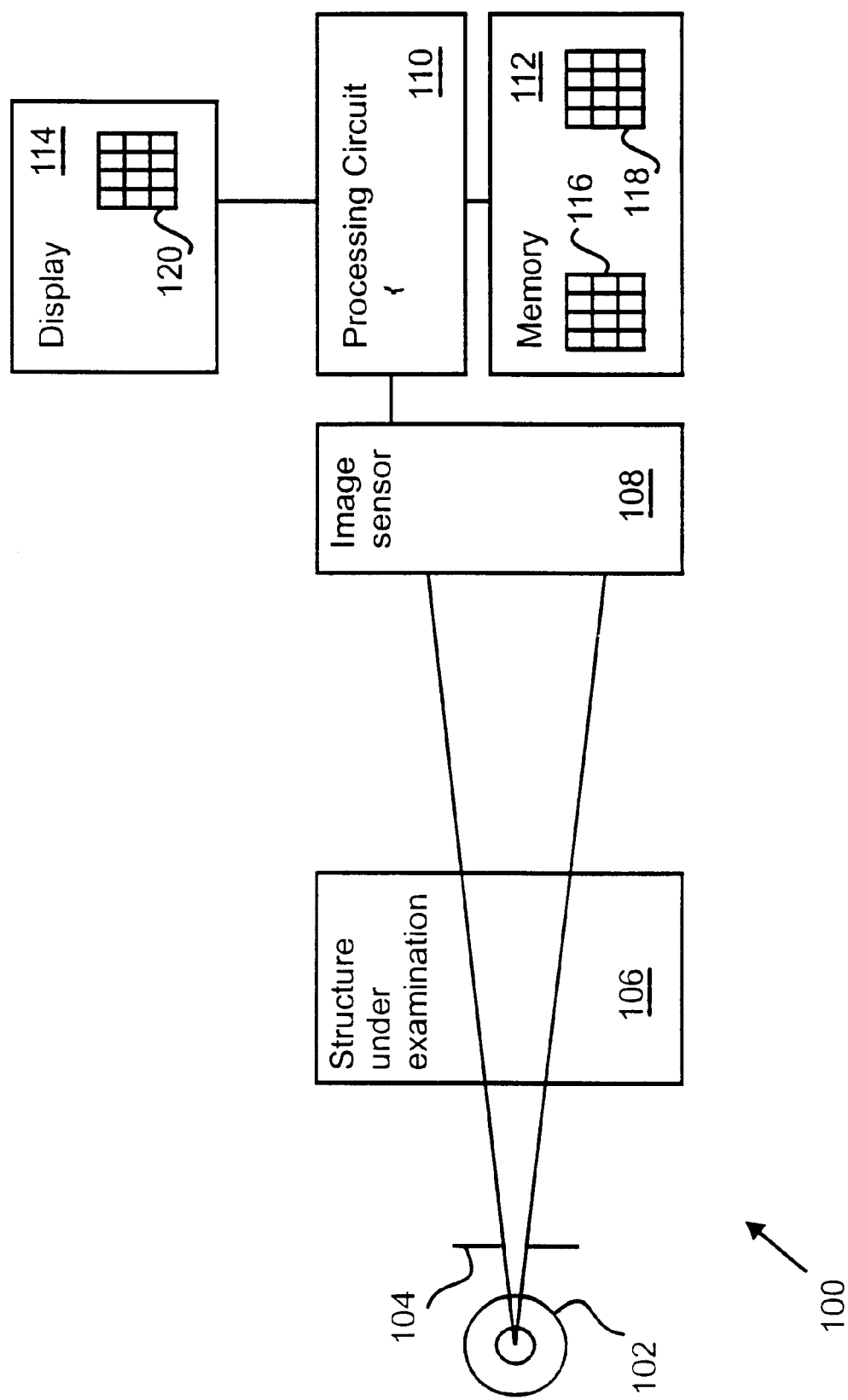
FIG. 1 illustrates a high level diagram of an X-ray imaging system.

Turning now to FIG. 1, that figure illustrates an X-ray imaging system 100. The imaging system 100 includes an X-ray source 102 and a collimator 104, which subject structure under examination 106 to X-ray photons. As examples, the X-ray source 102 may be an X-ray tube, and the structure under examination 106 may be a human patient, test phantom or other inanimate object under test.

The X-ray imaging system 100 also includes an image sensor 108 coupled to a processing circuit 110. The processing circuit 110 (e.g., a microcontroller, microprocessor, custom ASIC, or the like) couples to a memory 112 and a display 114. The memory 112 (e.g., including one or more of a hard disk, floppy disk, CDROM, EPROM, and the like) stores a high energy level image 116 (e.g., an image read out from the image sensor 108 after 110–140 kVp 5 mAs exposure) and a low energy level image 118 (e.g., an image read out after 70 kVp 25 mAs exposure). The memory 112 also stores instructions for execution by the processing circuit 110, as explained below, to cancel certain types of structure in the images 116–118 (e.g., bone or tissue structure). A structure cancelled image 120 is thereby produced for display. The image sensor 108 may be a flat panel solid state image sensor, for example, although conventional film images stored in digital form in the memory 112 may also be processed as disclosed below as well.

The processing circuit 110 uses a log subtraction technique to decompose spatially registered images from the structure under examination 106 into constituent materials (e.g., bone and soft tissue in chest X-ray images). To this end, a high energy level image and a low energy level image are obtained and processed according to:

$$SB(x,y)=\exp[\log(H(x,y))-w\,\log(L(X\,x,y))], (0<w<1) \quad (1)$$

where SB is the decomposed image achieved through the log subtraction at a specific cancellation parameter w, H(x,y) is the high energy level image, and L(x,y) is the low energy level image. By varying w, SB becomes a decomposed image of either soft tissue or of bone.

The processing circuit 110 iteratively varies the cancellation parameter w in Equation (1), obtains a structure cancelled image (i.e., SB(x,y)) according to Equation (1), and evaluates a cancellation metric from the structure cancelled image. The processing circuit then selects a provisional cancellation parameter based on the cancellation metric.

More specifically, the processing circuit 110 minifies H(x,y) and L(x,y) (i.e., reduces their size through neighborhood averaging, for example), and uses Equation (1) at varying w to create multiple images of SB(x,y). The parameters for Equation (1) may be selected based on empirical knowledge of image acquisition parameters. For example, if H(x,y) and L(x,y) are obtained at 140 kVp, 5 mAs and 70 kVp, 25 mAs, a starting cancellation parameter, w, may be 0.2 and the step size may be 0.05. On the other hand, if H(x,y) and L(x,y) are obtained at 110 kVp, 5 mAs, and 70 kVp, 25 mAs, a starting value of the cancellation parameter may be 0.4 and the step size may be 0.04. The cancellation parameter may then be varied between a range of 0.3 and 0.95, or other ranges empirically determined.

Note that no particular magnitude of difference in the first energy level and the second energy level is required. The iterative determination of the cancellation parameter proceeds independently of the energy levels used.

The images H(x,y) and L(x,y) may vary depending on the type of structure sought to be cancelled. For example, if bone is to be cancelled, then H(x,y) and L(x,y) may be 64×64 pixel images of a portion of the spine (or other predominately bone structure). If tissue is to be cancelled, then H(x,y) and L(x,y) may be 256×256 images of a lung region between ribs (or other predominately tissue area).

At each step, a cancellation metric (e.g., variance in SB(x,y)) is determined. The variance will be lowest at the value of w achieves the most cancellation of bone (for H(x,y) and L(x,y) images of bone structure) or of tissue (for H(x,y) and L(x,y) images of tissue structure). The lowest variance is selected as a provisional cancellation parameter and may be used to cancel similar structure in other images. Preferably, however, the processing circuit 110 performs one or more additional iterations at smaller step sizes around the provisional cancellation parameter.

For example, the new step size may be 0.01, and new SB(x,y) images are then computed according to Equation (1) on either side of the provisional cancellation parameter. The processing circuit 110 determines the variance in each SB(x,y) to select a final cancellation parameter that best cancels bone or tissue. It is noted that higher resolution H(x,y) and L(x,y) images may be used during the additional iterations.

The process identified above may further automated through the use of a histogram technique. In particular, the processing circuit 110 may employ a pattern recognition algorithm to identify the chest cage, spine, and ribs. In the central region of a standard posterior-anterior image, a larger X-ray absorption region in the middle of horizontal rib lines (or the average of horizontal rib lines) represents the spine. Away from the spine, periodic high transmission intensities in vertical lines represent unobstructed lung, while a lower X-ray transmission represents ribs.

Thus, an intensity histogram may be constructed to identify two lungs based on pixel intensity. A profile drawn across the lungs will include two peaks (one for each lung), and a valley (corresponding to the spine). The peaks and valleys then identify structure from which H(x,y) and L(x,y) may be taken as predominately bone (e.g., the spine) or tissue (e.g., the lung).

It is also noted that the processing circuit 110 may first remove background radiation from the H(x,y) and L(x,y) images before selecting a cancellation parameter. To this end, the processing circuit 110 may use regions of air (e.g., regions between the chest and arm, or above the shoulders) identified, for example, in an image or in the intensity histogram to determine a background radiation level. The background radiation level may then be subtracted from H(x,y) and L(x,y).

Figure 2:
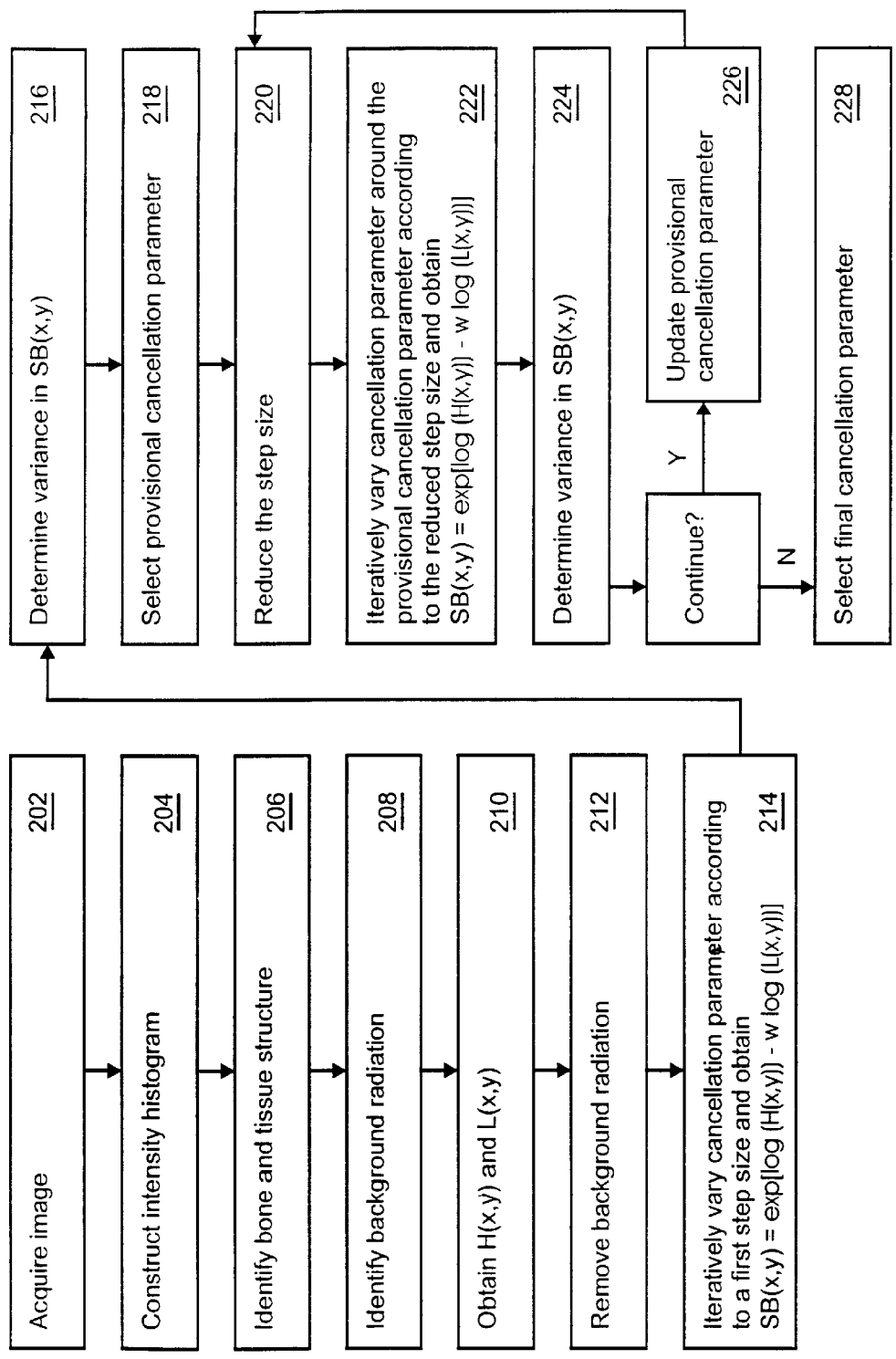
FIG. 2 illustrates a flow diagram for the operation of the X-ray imaging system.

Turning next to FIG. 2, that figure present a flow diagram 200 that shows the processing steps that occur at the processing circuit 110. First, the processing circuit 110 acquires an image (202) an prepares an intensity histogram (204). Bone and tissue structure, as well as background radiation are identified (steps 206–208). Subsequently, the processing circuit 110 obtains H(x,y) and L(x,y) through a high and low energy imaging selection (step 210) and removes background radiation, if desired, from H(x,y) and L(x,y) (step 212).

Continuing at step 214, the processing circuit iteratively varies the cancellation parameter, w, according to a first step size and evaluates Equation (1) to obtain a structure cancelled image SB(x,y). The variance in SB(x,y) is determined (step 216) and a provisional value for the cancellation parameter is selected (step 218). Subsequently, at step 220, the processing circuit 110 reduces the step size, and iteratively evaluates Equation (1) by varying the cancellation parameter around the provisional value (step 222) by the reduced step size.

Similarly, at step 224, the processing circuit determines the variance in SB(x,y). At the end of the iterations, the provisional cancellation parameter may be updated (step 226) and additional iterations performed with smaller step sizes. Alternatively, the processing circuit may instead select a final value for the cancellation parameter that yields the minimum variance in SB(x,y) (step 228).

Thus, the present invention provides an automated technique for selecting a value for a cancellation parameter that best eliminates structure (e.g., bone or tissue) from an image. The final value of the cancellation parameter may thus be obtained without significant trial and error delays, or subject to possible operator biases. The cancellation parameter may then be used to cancel the same structure in subsequently obtained images. The software underlying the processing steps shown in FIG. 2 for the X-ray imaging system 100 may be stored on a computer readable medium (such as the memory types identified above) for convenient distribution.

While the invention has been described with reference to a preferred embodiment, those skilled in the art will understand that various changes may be made and equivalents may be substituted without departing from the scope of the invention. In addition, many modifications may be made to adapt a particular step, structure, or material to the teachings of the invention without departing from its scope. Therefore, it is intended that the invention not be limited to the particular embodiment disclosed, but that the invention will include all embodiments falling within the scope of the appended claims.

What is claimed is:

1. A method for determining a cancellation parameter for a dual energy decomposition, the method comprising:

obtaining a first energy level image of internal structure;

obtaining a second energy level image of the internal structure at an energy level lower than the first energy level image;

iteratively varying a cancellation parameter in a cancellation equation, obtaining a structure cancelled image from the first and second energy level images according to the cancellation equation, and evaluating a cancellation metric from the structure cancelled image; and selecting a provisional cancellation parameter based on the cancellation metric.

2. The method of claim 1, wherein the internal structure is predominately bone structure, and the cancellation metric is a bone cancellation metric.

3. The method of claim 2, wherein the internal structure comprises a portion of a spinal column.

4. The method of claim 1, wherein the internal structure is predominately soft tissue structure, and the cancellation metric is a soft tissue cancellation metric.

5. The method of claim 4, wherein the internal structure comprises a portion of a lung.

6. The method of claim 1, wherein the cancellation equation is:

$$SB(x,y)=\exp[\log(H(x,y))-w\ \log(L(x,y))],$$

and w is the cancellation parameter.

7. The method of claim 1, wherein the first and second energy level differ by at least 40 kVp.

8. The method of claim 7, wherein the first and second energy level differ by at least 70 kVp.

9. The method of claim 1, wherein the cancellation metric is variance in the structure cancelled image.

10. The method of claim 1, wherein iteratively varying comprises iteratively varying the cancellation parameter by a first step size over a predetermined range.

11. The method of claim 10, further comprising, subsequent to the selecting step, the steps of:

selecting a second step size smaller than the first step size;

iteratively varying the cancellation parameter in the cancellation equation around the provisional cancellation parameter by the second step size, obtaining a structure cancelled image from the first and second energy level images according to the cancellation equation, and evaluating the cancellation metric from the structure cancelled image; and selecting a final cancellation parameter based on the cancellation metric.

12. The method of claim 11, further comprising the step of subsequently canceling structure in additional images using the cancellation equation and the final cancellation parameter.

13. The method of claim 1, further comprising the step of subsequently canceling structure in additional images using the cancellation equation and the provisional cancellation parameter.

14. An image processing system for medical diagnostic imaging, the image processing system comprising:

a processing circuit;

a memory coupled to the processing circuit, the memory comprising storage for a first energy level image of internal structure and a second energy level image of the internal structure at an energy level lower than the first energy level image, the memory further comprising instructions for execution by the processor for:

iteratively varying a cancellation parameter in a cancellation equation, obtaining a structure cancelled image from the first and second energy level images according to the cancellation equation, and evaluating a cancellation metric from the structure cancelled image; and selecting a provisional cancellation parameter based on the cancellation metric.

15. The image processing system of claim 14, wherein the memory further comprises instructions for obtaining the first and second energy level images from an X-ray detector.

16. The image processing system of claim 14, wherein the internal structure is predominately bone structure, and the cancellation metric is a bone cancellation metric.

17. The image processing system of claim 16, wherein the internal structure comprises a portion of a spinal column.

18. The image processing system of claim 14, wherein the internal structure is predominately tissue structure, and the cancellation metric is a tissue cancellation metric.

19. The method of claim 18, wherein the internal structure comprises a portion of a lung.

20. The image processing system of claim 14, wherein the cancellation equation is:

$$SB(x,y)=\exp[\log 0(H(x,y))-w\ \log(L(x,y))],$$

and w is the cancellation parameter.

21. The image processing system of claim 14, wherein the cancellation metric is variance in the structure cancelled image.

22. The image processing system of claim 14, wherein the instructions for iteratively varying comprise instructions for iteratively varying the cancellation parameter by a first step size over a predetermined range.

23. The image processing system of claim 22, wherein the memory further stores instructions for:

selecting a second step size smaller than the first step size;

iteratively varying the cancellation parameter in the cancellation equation around the provisional cancellation parameter by the second step size, obtaining a structure cancelled image from the first and second energy level images according to the cancellation equation, and evaluating the cancellation metric from the structure cancelled image; and selecting a final cancellation parameter based on the cancellation metric.

24. The image processing system of claim 23, wherein the memory further stores instructions for subsequently canceling structure in additional images using the cancellation equation and the final cancellation parameter.

25. The image processing system of claim 14, wherein the memory further stores instructions for subsequently canceling structure in additional images using the cancellation equation and the provisional cancellation parameter.

26. The image processing system of claim 14, wherein the first and second energy level differ by at least 40 kVp.

27. The image processing system of claim 26, wherein the first and second energy level differ by at least 70 kVp.

28. A computer program product for structure cancellation in images of internal structure, the product comprising:

a storage medium readable by a processing circuit and storing instructions for execution by the processing circuit for:

iteratively varying a cancellation parameter in a cancellation equation, obtaining a structure cancelled image according to the cancellation equation from a first energy level image obtained at a first energy level and a second energy level image obtained at a second energy level different than the first energy level, and evaluating a cancellation metric from the structure cancelled image; and selecting a provisional cancellation parameter based on the cancellation metric.

29. The computer program product of claim 28, wherein the internal structure is predominately one of tissue and bone structure, and the cancellation metric is variance in the structure cancelled image.

30. The computer program product of claim 28, wherein the cancellation equation is:

$$SB(x,y)=\exp[\log(H(x,y))-w \log(L(x,y))],$$

and w is the cancellation parameter.

31. The computer program product of claim 28, wherein the instructions for iteratively varying comprise instructions for iteratively varying the cancellation parameter by a first step size over a predetermined range.

32. The computer program product of claim 31, wherein the storage medium further stores instructions for:

selecting a second step size smaller than the first step size;

iteratively varying the cancellation parameter in the cancellation equation around the provisional cancellation parameter by the second step size, obtaining a structure cancelled image from the first and second energy level images according to the cancellation equation, and evaluating the cancellation metric from the structure cancelled image; and selecting a final cancellation parameter based on the cancellation metric.

33. The computer program product of claim 32, wherein the storage medium further stores instructions for subsequently canceling structure in additional images using the cancellation equation and the final cancellation parameter.

34. The computer program product of claim 28, wherein the storage medium further stores instructions for subsequently canceling structure in additional images using the cancellation equation and the provisional cancellation parameter.

35. The computer program product of claim 28, wherein the first and second energy level differ by at least 40 kVp.

36. The computer program product of claim 35, wherein the first and second energy level differ by at least 70 kVp.

* * * * *